US00PP25443P2

(12) United States Plant Patent
Brown

(10) Patent No.: US PP25,443 P2
(45) Date of Patent: Apr. 14, 2015

(54) ***ABUTILON* PLANT NAMED 'NUABRED'**

(50) Latin Name: *Abutilon×hybrida*
Varietal Denomination: NUABRED

(71) Applicant: Graham Brown, Pennant Hills (AU)

(72) Inventor: Graham Brown, Pennant Hills (AU)

( * ) Notice: Subject to any disclaimer, the term of this patent is extended or adjusted under 35 U.S.C. 154(b) by 124 days.

(21) Appl. No.: 13/815,372

(22) Filed: Feb. 25, 2013

Related U.S. Application Data

(60) Provisional application No. 61/634,368, filed on Feb. 27, 2012.

(51) Int. Cl.
*A01H 5/00* (2006.01)

(52) U.S. Cl.
USPC ..... Plt./263.1

(58) Field of Classification Search
USPC ..... Plt./226, 263.1
See application file for complete search history.

(56) References Cited

PUBLICATIONS

Lucky Lantern *Abutilon* Red ('Nuabred'), Plant Haven, 2009.*

* cited by examiner

*Primary Examiner* — Anne Grunberg
(74) *Attorney, Agent, or Firm* — Barbara Campbell; Cochran Freund & Young LLC

(57) ABSTRACT

A new cultivar of *Abutilon* named 'NUABRED' that is characterized by a compact habit, medium green leaves, scarlet red flowers with prominent cream-green calyces, and a long blooming season. In combination these traits set 'NUABRED' apart from all other existing varieties of Abutilon known to the inventor.

2 Drawing Sheets

Genus: *Abutilon.*
Species: ×*hybrida.*
Denomination: 'NUABRED'.

BACKGROUND OF THE INVENTION

The present invention relates to a new and distinct cultivar of *Abutilon×hybrida*, commonly known as Chinese lantern. The new cultivar is in the family Malvaceae. Known botanically as *Abutilon×hybrida* the new variety will be referred to hereinafter by the cultivar name 'NUABRED'.

'NUABRED' is the result of a breeding program that commenced in 2000 in Pennant Hills, New South Wales, Australia. The objectives of the breeding program are to develop compact forms of *Abutilon* with significantly improved flowering characteristics, particularly a long flowering period, floriferous nature, and a wide range of flower color presented well at the time of sale.

'NUABRED' is a seedling selection resulting from the controlled cross-pollination of two parents which had been raised and retained by the inventor for breeding purposes. The female parent is an individual seedling known to the inventor as X05.5 (unreleased and unpatented). The male parent is an individual seedling known to the inventor as X05.1 (unreleased and unpatented). Cross-pollination was conducted by the inventor during 2006. The resulting seed was collected and sown by the inventor in January 2007, then grown out. In December 2007 the inventor selected 'NUABRED' based on the breeding objectives.

'NUABRED' is distinguishable from the parent selections by plant size and habit and by flower color. Both parent selections exhibit large leaves and less compact habit when compared with 'NUABRED'. Whereas the flower color of 'NUABRED' is scarlet red in color, the flowers of the female parent are darker red in color and the flowers of the male parent are smaller in size.

The closest comparison plant in commerce known to the inventor would be a seedling of similar flower color (if available) which can be raised from the Bella series of *Abutilon*, which is a seed strain. There are no named cultivars in this series which does not have the longevity of flowering period which is a characteristic of 'NUABRED' which appears to be sterile.

'NUABRED' exhibits compact habit, bell-shaped blooms that are scarlet red in color, with prominent cream-green calyces and medium sized green leaves. Flowers have a long flowering season, blooming from spring through fall. 'NUABRED' is suitable for use in containers and in the garden and landscape, performing best in well-drained soil and full sun with moderate water. Trimming stems when young, and after blooming, encourages strong basal branching and re-blooming. After one year of growth, a plant of 'NUABRED' achieves 50 cm. in height and 40 cm. in width. As a mature plant, the dimensions of 'NUABRED' are 80 cm. in height and 70 cm. in width. Other than hibiscus beetle and whitefly which are attracted to the genus, 'NUABRED' does not exhibit any notable susceptibility or resistance to pests and diseases. 'NUABRED' is hardy in USDA Zone 8, and tolerant of heat and drought once established.

'NUABRED' was first asexually propagated by the inventor in December 2007 in Macquarie Fields, New South Wales, Australia. Asexual propagation was accomplished using softwood cuttings. Since that time, under careful observation, the distinguishing characteristics of 'NUABRED' have been determined stable and uniform, and to reproduce true to type in successive generations of asexual propagation.

SUMMARY OF THE INVENTION

The following represent the distinguishing characteristics of the new *Abutilon* cultivar named 'NUABRED'. In combination these traits set 'NUABRED' apart from all other existing varieties of *Abutilon* known to the inventor. 'NUABRED' has not been tested under all possible conditions and phenotypic differences may be observed with variations in environmental, climatic, and cultural conditions, however, without any variance in genotype.

1. 'NUABRED' is perennial in temperatures above 15° Fahrenheit.
2. The growth habit of 'NUABRED' is compact due to its short internodes and freely branching structure.
3. 'NUABRED' achieves a height of 50 cm. and a spread of 40 cm. in the first year of growth.
4. 'NUABRED' achieves a height of 80 cm. and a spread of 70 cm. at maturity.
5. The stems of 'NUABRED' are strong and rigid.
6. The flowers of 'NUABRED' are bell-shaped facing downward and outward.
7. The flowers of 'NUABRED' are scarlet red in color.
8. The calyces of 'NUABRED' are prominent cream-green in color.
9. 'NUABRED' appears to be sterile and blooms from spring through fall.

BRIEF DESCRIPTION OF THE DRAWINGS

The accompanying color drawings illustrate the overall appearance of the new *Abutilon* cultivar named 'NUABRED' showing color of the foliage and flower as true as is reasonably possible to obtain in color reproductions of this type.

The drawing labeled

Drawing labeled

Figure 1:
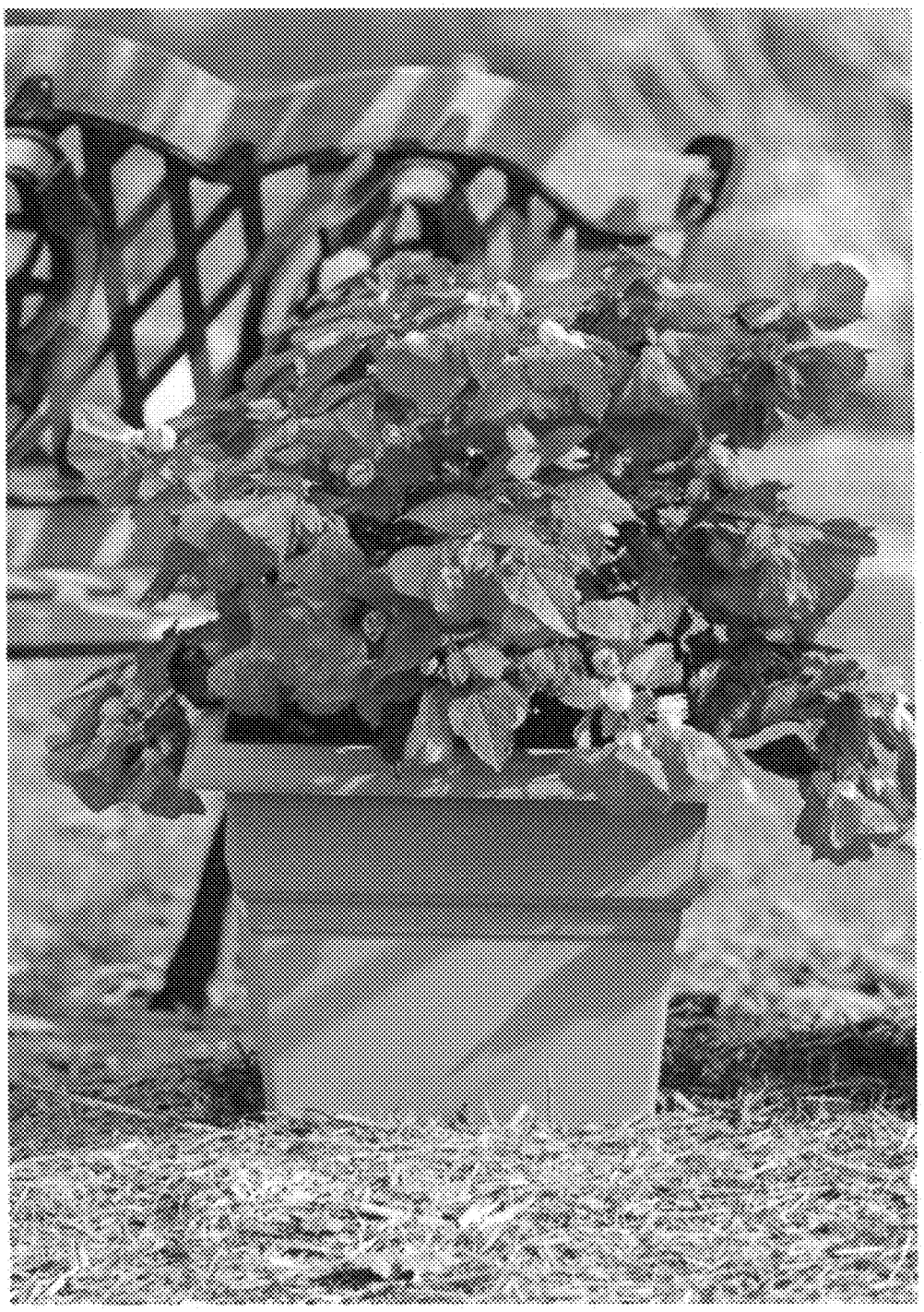
FIG. 1 depicts a whole plant of 'NUABRED'.
Figure 2:
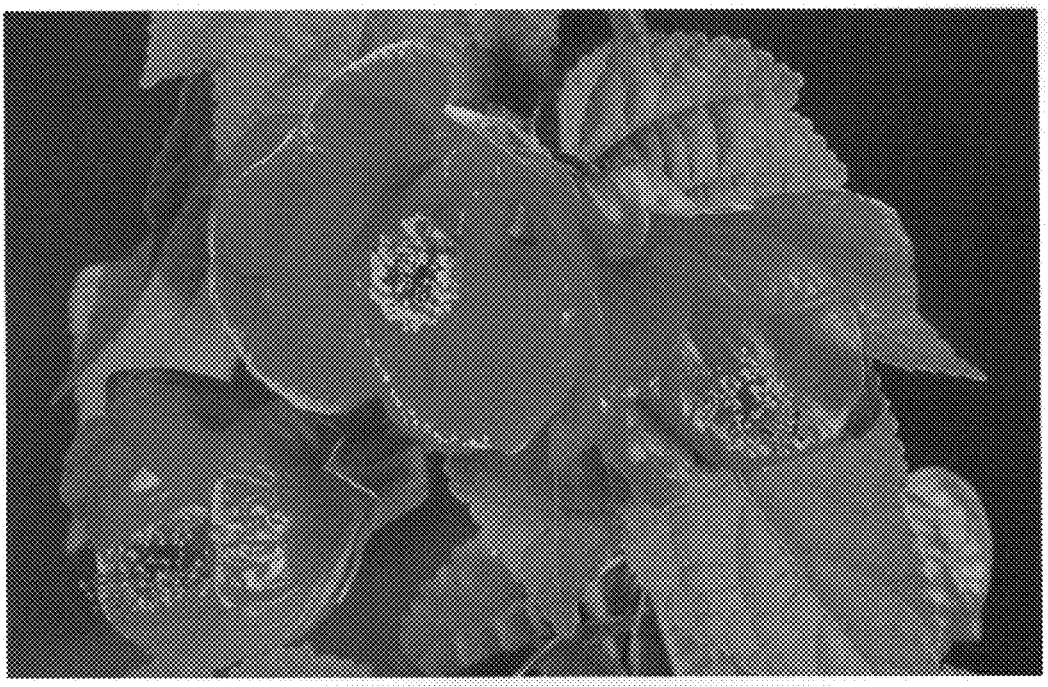
FIG. 2 depicts a close-up view of the scarlet red flowers of 'NUABRED' and their cream-green calyces.

The drawings are made using conventional techniques and although foliage color may appear different from actual colors due to light reflectance, they are as accurate as possible by conventional photography.

BOTANICAL DESCRIPTION OF THE PLANT

The following is a detailed description of the *Abutilon* cultivar named 'NUABRED'. Data was collected in Santa Barbara, Calif. from one year old plants grown outdoors in 1-litre containers. Color determinations are in accordance with The Royal Horticultural Society Colour Chart 2007 except where general color terms of ordinary dictionary significance are used. The growing requirements are similar to the species.

Botanical classification: *Abutilon*×*hybrida* 'NUABRED'.
Family: Malvaceae.
Genus: *Abutilon*.
Species: ×*hybrida*.
Denomination: 'NUABRED'.
Common name: Chinese lantern.
Use: Pot and container, garden border, and modern landscape.
Parentage: *Abutilon*×*hybrida* 'NUABRED' is a seedling selection resulting from the deliberate controlled cross-pollination of the following parents:
- *Female parent*.—An individual *Abutilon* X05.5 (unpatented).
- *Male parent*.—An individual *Abutilon* X05.1 (unpatented).

Vigor: Vigorous.
Growth habit: Compact.
Dimensions first year: 50 cm in height and 40 cm in width.
Dimensions at maturity: 80 cm in height and 70 cm in width.
Hardiness: USDA Zone 8.
Propagation: Softwood cuttings.
Root system: Fine and fibrous.
Cultural requirements: Plant in full sun and well-drained soils with moderate water, drought tolerant once established.
Type: Perennial.
Time to initiate roots (range): 14-28 days to produce roots on an initial cutting.
Crop time (range): 6-8 weeks to produce a 4-inch container plant from a 72 cell transplant (spring planting) and 10-12 weeks to produce a 1-litre container plant from a 72 cell transplant (spring planting).
Seasonal interest: Showy flowers and calyces spring through fall.
Pests and diseases: Other than hibiscus beetle and whitefly which are attracted to the genus, 'NUABRED' does not exhibit any notable susceptibility or resistance to pests and diseases.
Special considerations: Trim back when young and after blooming to encourage strong basal branching and re-blooming.

Stem:
- *Branching habit*.—Freely branching.
- *Stem length* (*range*).—15 cm to 23 cm.
- *Stem diameter*.—0.40 cm.
- *Stem texture*.—Soft woody.
- *Stem strength*.—Strong and rigid.
- *Internode length* (*average*).—2 cm.
- *Shape*.—Cylindrical.
- *Surface*.—Glabrous.
- *Branch color*.—138B.

Foliage:
- *Leaf arrangement*.—Alternate.
- *Leaf division*.—Simple.
- *Leaf margin*.—Crenate.
- *Leaf shape* (*range*).—Cordate to ovate.
- *Leaf base*.—Cordate.
- *Leaf apex*.—Acute.
- *Leaf venation*.—Pinnate and reticulate.
- *Vein color* (*adaxial surface*).—145B.
- *Vein color* (*abaxial surface*).—145B.
- *Leaf surface* (*adaxial*).—Pubescent.
- *Leaf surface* (*abaxial*).—Pubescent with veins lanate.
- *Leaf texture*.—Velutinous.
- *Leaf attachment*.—Petiolate.
- *Petiole dimensions* (*average*).—2.50 cm in length and 1 mm in width.
- *Petiole color*.—147B.
- *Petiole surface*.—Puberulent.
- *Leaf length* (*range*).—5.5-7 cm.
- *Leaf width* (*range*).—1.5-5 cm.
- *Leaf color* (*adaxial surface*).—137A.
- *Leaf color* (*abaxial surface*).—N138B.
- *Stipules*.—Present.
- *Stipule color*.—145B.
- *Stipule dimensions*.—4 mm in length and 3 mm in diameter.
- *Stipule apex*.—Acute.
- *Foliar fragrance*.—Absent.

Inflorescence:
- *Type*.—Cyme.
- *Dimensions of inflorescence* (*average*).—4 cm in length and 10 cm in width.

*Quantity of flowers per inflorescence* (*range*).—3-4 per cyme.
*Flower arrangement*.—Clustered.
*Flower shape*.—Campanulate.
*Flower diameter* (*range*).—4.50 cm-5.00 cm.
*Flower depth* (*average*).—4.50 cm.
*Aspect*.—Pendulous.
*Persistent or self-cleaning*.—Self-cleaning
*Bud color*.—145A.
*Bud shape*.—Ovoid.
*Bud length* (*range*).—1.10 cm to 1.60 cm.
*Bud diameter* (*range*).—1.00 cm to 1.50 cm.
*Bud apex*.—Acute.
*Bud surface*.—Pubescent.
*Petals*.—Five in number.
*Petal shape*.—Obdeltoid.
*Petal apex*.—Obtuse.
*Petal base*.—Attenuate.
*Petal length*.—3.60 cm.
*Petal width*.—3.50 cm.
*Petal margin*.—Entire and involute.
*Petal color* (*abaxial surface*).—45A.
*Petal color* (*adaxial surface*).—45A.
*Petals unfused or fused*.—Unfused and individually adnate to stamen column.
*Petal surface* (*abaxial and adaxial surface*).—Glabrous.
*Epicalyx*.—Absent.
*Calyx shape*.—Lobed.
*Calyx color* (*dorsal and ventral surfaces*).—145C.
*Calyx surface* (*dorsal and ventral*).—Pubescent.
*Calyx dimensions*.—2.50 cm in diameter and 1.50 cm in length.
*Lobes*.—5 in number.
*Lobe dimensions*.—1 cm in length and 0.75 cm in width.
*Lobe apex*.—Broad acute.
*Lobe base*.—Truncate.
*Lobes fused or unfused*.—Basally fused.
*Lobe margin*.—Entire.
*Blooming season*.—Spring through fall.
*Peduncle arrangement*.—Axillary.
*Peduncle shape*.—Cylindrical.
*Peduncle length*.—1 cm to 2 cm.
*Peduncle width*.—1 mm.
*Peduncle color*.—146D.
*Peduncle surface*.—Flocculent.
*Flower fragrance*.—Absent.

Reproduction organs:
*Stamens*.—Many filaments connate into hollow stamen column.
*Stamen column color*.—9A.
*Stamen column dimensions*.—3 cm in length and 2 mm in diameter.
*Stamen column surface*.—Fluted and glabrous.
*Anther*.—Approximately 75 in number.
*Anther color*.—16A.
*Shape of anther*.—Crescent-shaped.
*Dimensions of anther*.—4 mm in length and less than 0.50 mm in diameter.
*Pollen quantity*.—Heavy.
*Pollen color*.—16A.
*Style*.—5 in number, many enclosed within stamen column.
*Stigma number* (*average*).—9 in number.
*Stigma*.—Exserted and divided.
*Stigma color*.—34B; except lower one-third of length, N34D.
*Stigma dimensions*.—2 cm in length and less than 0.50 mm in diameter.
*Ovary position*.—Superior.
*Ovary shape*.—Conic.
*Ovary color*.—145D.
*Ovary dimensions*.—6 mm in height and 3 mm in width.

Seed: None observed to date.

The invention claimed is:

1. A new and distinct variety of *Abutilon* plant named 'NUABRED' as described and illustrated.

* * * * *